United States Patent [19]

Biftu

[11] Patent Number: 5,447,717

[45] Date of Patent: Sep. 5, 1995

[54] CHOLESTEROL-LOWERING AGENTS

[75] Inventor: Tesfaye Biftu, Westfield, N.J.

[73] Assignee: Merck & Co., Inc., Rahway, N.J.

[21] Appl. No.: 23,029

[22] Filed: Feb. 25, 1993

[51] Int. Cl.[6] .......................................... A61K 31/335
[52] U.S. Cl. ................... 424/78.12; 514/452; 549/263; 549/328; 424/78.16
[58] Field of Search ............ 549/263, 328; 514/452; 424/78.16, 78.12

[56] References Cited

U.S. PATENT DOCUMENTS

| | | | |
|---|---|---|---|
| 4,308,209 | 12/1981 | Buendia et al. | 549/263 |
| 5,025,003 | 6/1991 | Biller | 514/120 |
| 5,026,554 | 6/1991 | Bartizal et al. | 424/404 |
| 5,053,425 | 10/1991 | Bartizal et al. | 514/452 |
| 5,055,487 | 10/1991 | Bartizal et al. | 514/452 |
| 5,096,923 | 3/1992 | Bergstrom et al. | 514/452 |
| 5,102,907 | 4/1992 | Bergstrom et al. | 514/456 |
| 5,132,320 | 7/1992 | Bergstrom et al. | 514/452 |

FOREIGN PATENT DOCUMENTS

| | | |
|---|---|---|
| 512865 | 5/1982 | European Pat. Off. |
| 448393 | 3/1991 | European Pat. Off. |
| 450812 | 3/1991 | European Pat. Off. |
| 475706 | 9/1991 | European Pat. Off. |
| 494622 | 1/1992 | European Pat. Off. |
| 503520 | 3/1992 | European Pat. Off. |
| WO92/12156 | 1/1992 | WIPO |
| WO92/12157 | 1/1992 | WIPO |
| WO92/12158 | 1/1992 | WIPO |
| WO92/12159 | 1/1992 | WIPO |
| WO92/12160 | 1/1992 | WIPO |
| WO92/16530 | 3/1992 | WIPO |

OTHER PUBLICATIONS

Baxter et al., J. Biol. Chem 267, 11705–11708, (1992).

Primary Examiner—C. Warren Ivy
Assistant Examiner—Raymond Covington
Attorney, Agent, or Firm—Carol S. Quagliato; Catherine D. Fitch

[57] ABSTRACT

This invention relates to compounds of structural formula (I):

$$R^4(A)_a-O \quad OR^5 \quad (I)$$
$$Z^2OC \quad \quad R^1$$
$$Z^1OC$$

which are squalene synthase inhibitors and thus useful as cholesterol lowering agents and antifungal agents. These compounds are also inhibitors of farnesyl protein transferass and farnesylation of the oncogene protein Ras and thus useful in treating cancer.

7 Claims, No Drawings

CHOLESTEROL-LOWERING AGENTS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR ® (lovastatin) and ZOCOR ®, now commercially available, are members of a group of very active antihypercholesterolemic agents that function by limiting cholesterol biosynthesis by inhibiting the enzyme HMG-CoA reductase.

Squalene synthase (also called squalene synthetase) is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthase have employed pyrophosphate or pyrophosphate analog containing compounds such as those described in P. Ortiz de Montellano et al., J. Med. Chem. 20, 243 (1977), E.J. Corey and R. Volante, J. Am. Chem. Soc., 98, 1291 (1976), and U.S. Pat. No. 5,025,003 to S. Billet. U.S. Pat. No. 4,871,721 to S. Billet describes isoprenoid(phosphinylmethyl) phosphonates as inhibitors of squalene synthase.

U.S. Pat. Nos. 5,096,923; 5,026,554; and 5,102,907 disclose non-phosphorus-containing substituted 2,8-dioxabicyclo-[3.2.1] octane derivatives useful as squalene synthase inhibitors.

Recently it has been shown that certain natural product nonphosphorous containing inhibitors of squalene synthase and their esters are useful in inhibiting fungal growth. This utility is described in U.S. Pat No. 5,026,554.

The present invention is directed to compounds of structural formula (I) which are squalene synthase inhibitors for the inhibition of fungal growth.

The present invention is also directed to compounds of structural formula (I) which are inhibitors of farnesyl-protein transferass for inhibition of farnesylation of the oncogene protein Ras and the treatment of cancer. These compounds are inhibitors of farnesyl-protein transferass. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid: Reiss st. al., ibid; Reiss et al., PNAS, 88:732–736 (1991)). However, the reported inhibitors of farnesyl-transferase are metabolically unstable or inactive in cells.

Pharmaceutical compositions containing the compounds of this invention and methods of treatment utilizing these compositions for use in inhibiting farnesyl-protein transferase and farnesylation of the oncogene protein Ras are described herein.

The present invention provides nonphosphorus containing inhibitors of squalene synthase.

DETAILED DESCRIPTION OF THE INVENTION

The present invention is directed to novel compounds of structural formula (I) which are squalene synthase inhibitors:

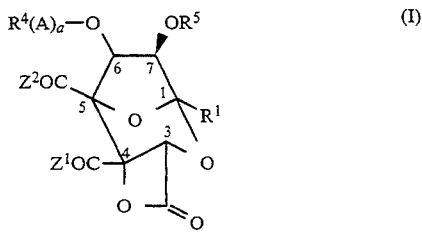

a is 0 or 1;

A is —C(O)—, —NR$^3$—C(O)—, or —OC(O)—;

R$^1$ is:
(1) C$_{1-20}$ alkyl,
(2) substituted C$_{1-20}$ alkyl wherein one or more of the carbons is substituted with X$^3$;
(3) C$_{1-20}$ alkyl wherein one or more of the carbons is replaced by —NR$^3$—, —O—, or —S(O)n—;
(4) substituted C$_{1-20}$ alkyl wherein one or more of the carbons is replaced by —NR$^3$—, —O— or —S(O)$_n$— and wherein one or more of the carbon atoms is substituted with X$^3$;
(5) aryl substituted with X and Y;
(6) heteroaryl substituted with X and Y;
(7) C$_{2-20}$ alkenyl wherein alkenyl contains one or more double bonds;
(8) substituted C$_{2-20}$ alkenyl wherein alkenyl contains one or more double bonds and wherein one or more of the carbons is substituted with X$^3$;
(9) C$_{2-20}$ alkenyl wherein alkenyl contains one or more double bonds and one or more of the nonolefinic carbons is replaced by —NR$^3$—, —O— or —S(O)$_n$—;
(10) substituted C$_{2-20}$ alkenyl wherein alkenyl contains one or more double bonds and one or more of the nonolefinic carbons is replaced by —NR$^3$—, —O— or —S(O)$_n$— and wherein one or more of the carbons is substituted with X$^3$;
(11) C$_{3-10}$cycloalkyl;
(12) substituted C$_{3-10}$cycloalkyl in which one or more of the carbon atoms is substituted with:
 (a) halogen,
 (b) hydroxy,
 (c) R$^3$R$^3$N—,
 (d) R$^2$O—,
 (e) R$^2$O—C(O)—,
 (f) R$^3$—C(O)—O—,
 (g) oxo,
 (h) C$_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) R$^3$—C(O)—NR$^3$—,
 (n) R$^3$R$^3$N—C(O)—, (o) $C_{1-10}$alkylS(O)$_n$—,
(p) $C_{1-10}$alkyl,
(q) —CO$_2$H,
(r) —vinylidene,
(s) $R^3$—C(O)—,
(t) $R^2$O—C(O)—O—,
(u) $R^3R^3$N—C(O)—O—, or
(v) $R^2$O—C(O)—NR$^3$—;

each $R^2$ is independently:
(1) $C_{1-10}$ alkyl;
(2) aryl substituted with X and Y;
(3) arylC$_{1-4}$ alkyl wherein aryl is substituted with X and Y;
(4) heteroaryl wherein heteroaryl is substituted with X and Y;
(5) heteroarylC$_{1-4}$ alkyl- wherein heteroaryl is substituted with X and Y;
(6) heterocycloalkylC$_{1-4}$alkyl—;
(7) C$_{2-10}$ alkenyl;
(8) arylC$_{2-10}$ alkenyl wherein aryl is substituted with X and Y; or
(9) C$_{3-10}$alkynyl;

each $R^3$ is independently:
(1) C$_{1-10}$alkyl;
(2) aryl substituted with X and Y;
(3) arylC$_{1-4}$ alkyl wherein aryl is substituted with X and Y;
(4) heteroaryl wherein heteroaryl is substituted with X and Y;
(5) heteroarylC$_{1-4}$ alkyl— wherein heteroaryl is substituted with X and Y;
(6) heterocycloalkylC$_{1-4}$ alkyl—;
(7) C$_{2-10}$ alkenyl;
(8) arylC$_{2-10}$ alkenyl wherein aryl is substituted with X and Y;
(9) C$_{3-10}$alkynyl;
(10) hydrogen; or
(11) C$_{1-5}$ alkyl substituted with X$^1$;

$R^4$ is:
(1) C$_{1-20}$ alkyl;
(2) substituted C$_{1-20}$alkyl in which one or more carbon atoms is substituted with X$^3$;
(3) C$_{1-20}$alkyl wherein one or more of the carbons is replaced by —NR$_3$—, —O—, or —S(O)n—;
(4) substituted C$_{1-20}$ alkyl wherein one or more of the carbons is replaced by —NR$^3$—, —O— or —S(O)$_n$— and wherein one or more carbon atoms is substituted with X$^3$;
(5) aryl substituted with X and Y;
(6) heteroaryl substituted with X and Y;
(7) C$_{2-20}$ alkenyl wherein alkenyl contains one or more double bonds;
(8) substituted C$_{2-20}$alkenyl wherein alkenyl contains one or more double bonds and wherein one or more of the carbons is substituted with X$^3$;
(9) C$_{2-20}$ alkenyl wherein alkenyl contains one or more double bonds and one or more of the nonolefinic carbons is replaced by —NR$^3$—, —O— or —S(O)$_n$—;
(10) substituted C$_{2-20}$ alkenyl wherein alkenyl contains one or more double bonds and one or more of the nonolefinic carbons is replaced by —NR$^3$—, —O— or —S(O)$_n$— and wherein one or more of the carbon atoms is substituted with X$^3$;
(11) C$_{3-10}$ cycloalkyl;
(12) substituted C$_{3-10}$ cycloalkyl in which one or more of the carbon atoms is substituted with X$^3$; or
(13) hydrogen;

$R^5$ is:
(1) hydrogen;
(2) C$_{1-10}$ alkyl;
(3) aryl substituted with X and Y;
(4) arylC$_{1-4}$ alkyl, wherein aryl is substituted with X and Y;
(5) $R^2$O—C(O)—;
(6) C$_{3-10}$ cycloalkyl;
(7) $R^3$—C(O)—; or
(8) $R^3R^3$N—C(O)—;

aryl including X, Y substitution is:

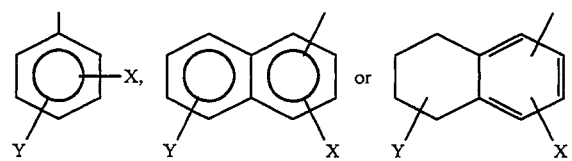

heteroaryl including X, Y substitution is

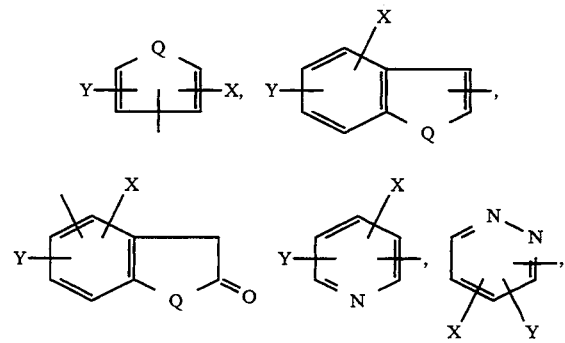

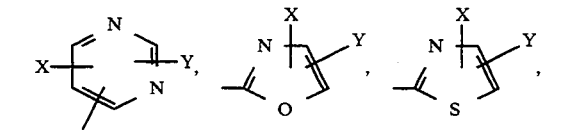

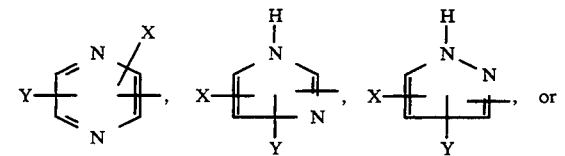

wherein:
Q is —NR$^3$, —O— or —S—;
heterocycloalkyl is:

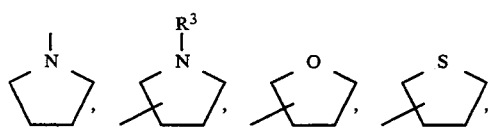

-continued

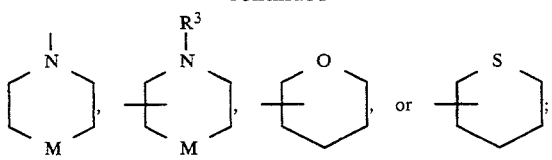

wherein:

M is —NR³, —O—, —S— or —CH₂—

X and Y are each independently:
(1) hydrogen;
(2) hydroxy;
(3) halogen;
(4) trifluoromethyl;
(5) $C_{1-10}$ alkyl;
(6) aryl substituted with $X^1$ and $Y^1$;
(7) $R^2O$—;
(8) arylcarbonylory—, wherein aryl is substituted With $X^1$ and $Y^1$;
(9) $R^3$—C(O)—O—;
(10) —$CO_2R^2$;
(11) —$CO_2H$; or
(12) nitro;

$X^1$ and $Y^1$ are each independently:
(1) hydrogen;
(2) hydroxy;
(3) halogen;
(4) trifluoromethyl;
(5) $C_{1-4}$ alkyl;
(6) $R^2O$—;
(7) $R^3$—C(O)—O—;
(8) —$CO_2R^2$;
(9) —$CO_2H$; or
(10) nitro;

each $X^3$ is independently:
(1) halogen
(2) hydroxy,
(3) $R^3R^3N$—,
(4) $R^2O$—,
(5) $R^2O$—C(O)—,
(6) $R^3$—C(O)—O—,
(7) oxo,
(8) $C_{3-10}$ cycloalkyl,
(9) aryl substituted with X and Y,
(10) heteroaryl substituted with and Y,
(11) heterocycloalkyl,
(12) aryl S(O)$_n$, wherein aryl is substituted with X and Y,
(13) $R^3$—C(O)—$NR^3$—,
(14) $R^3R^3N$—C(O)—,
(15) —$CO_2H$,
(16) —vinylidene,
(17) $R^3$—C(O)—,
(18) $R^2O$—C(O)—O—,
(19) $R^3R^3NOC(O)$—O—, or
(20) $R^2O$—C(O)—$NR^3$—;

n is 0,1 or 2;

$Z^1$ and $Z^2$ are each independently:
(1) —$OR^6$;
(2) —$SR^6$; or
(3) —$NR^6R^6$;

each $R^6$ is independently:
(1) $C_{1-20}$ alkyl;
(2) substituted $C_{1-20}$ alkyl in which one or more of the carbon atoms is substituted with $X^3$;
(3) $C_{1-20}$ alkyl wherein one or more of the carbons is replaced by —$NR^3$—, —O— or —S(O)$_n$—;
(4) substituted $C_{1-20}$ alkyl wherein one or more of the carbons is replaced by —$NR^3$—, —O— or —S(O)$_n$— and wherein one or more of the carbon atoms is substituted with $X^3$;
(5) $C_{2-20}$ alkenyl wherein alkenyl contains one or more double bonds;
(6) substituted $C_{2-20}$ alkenyl wherein alkenyl contains one or more double bonds and wherein one or more of the carbons is substituted with:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$ cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) $R^3$—C(O)—$NR^3$—,
(n) $R^3R^3N$—C(O)—,
(o) —$CO_2H$,
(p) —vinylidene,
(q) $R^3$—C(O)—,
(r) $R^2O$—C(O)—O—,
(s) $R^3R^3N$—C(O)—O—,
(t) $R^2O$—C(O)—$NR^3$—, or
(u) —OC(O)O—, which forms a five-membered ring:

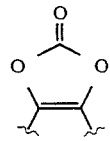

with adjacent olefinic carbons;
(7) $C_{2-20}$ alkenyl wherein alkenyl contains one or more double bonds and one or more of the nonolefinic carbons is replaced by —$NR^3$—, —O— or —S(O)$_n$—;
(8) substituted $C_{2-20}$ alkenyl wherein alkenyl contains one or more double bonds and one or more of the nonolefinic carbons is replaced by —$NR^3$—, —O— or —S(O)$_n$— and wherein one or more of the carbon atoms is substituted with:
(a) halogen
(b) hydroxy,
(c) $R^3R^3N$—,
(d) $R^2O$—,
(e) $R^2O$—C(O)—,
(f) $R^3$—C(O)—O—,
(g) OXO,
(h) $C_{3-10}$ cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) $R^3$—C(O)—$NR^3$—,
(n) $R^3R^3N$—C(O)—,
(o) —$CO_2H$, (p) —vinylidene,
(q) $R^3$—C(O)—,
(r) $R^2$O—C(O)—O—,
(s) $R^3R^3$N—C(O)—O—,
(t) $R^2$O—C(O)—$NR^3$— or
(u) —OC(O)O—, which forms a five-membered ring:

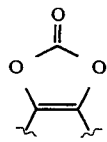

with adjacent olefinic carbons;

(9) $C_{2-20}$ alkynyl wherein alkynyl contains one or more triple bonds;
(10) substituted $C_{2-20}$ alkynyl wherein alkynyl contains one or more triple bonds and wherein one or more of the carbons is substituted with $X^3$;
(11) $C_{2-20}$ alkynyl wherein alkynyl contains one or more triple bonds and one or more of the saturated carbons is replaced by —$NR^3$—, —O— or —S(O)$_n$—;
(12) substituted $C_{2-20}$ alkynyl wherein alkynyl contains one or more double bonds and one or more of the saturated carbons is replaced by —$NR^3$—, —O— or —S(O)$_n$— and wherein one or more of the carbon atoms substituted with $X^3$;
(13) aryl substituted with X and Y;
(14) heteroaryl substituted with X and Y;
(15) $C_{3-5}$ cycloalkyl;
(16) substituted $C_{3-5}$ cycloalkyl in which one or more of the carbon atoms is substituted with:
   (a) $R^3$O—, or
   (b) $R^3R^3$N—; or
(17) hydrogen;
or a pharmaceutically acceptable salt.

In one embodiment of this invention are the compounds of formula (I) having a structural formula selected from:

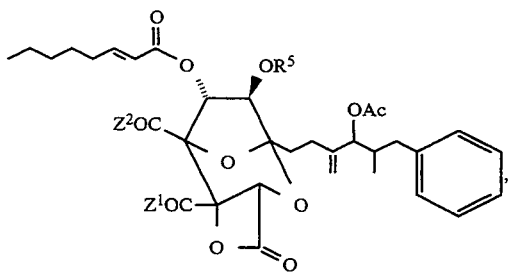

IA

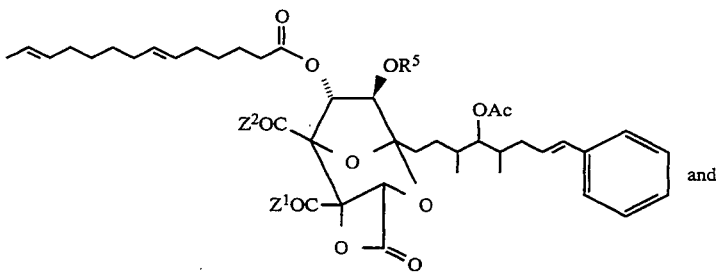

IB and

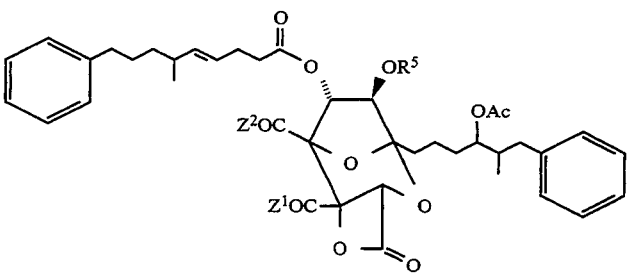

IC

A second embodiment of this invention is further limited to compounds having the structural formula (III):

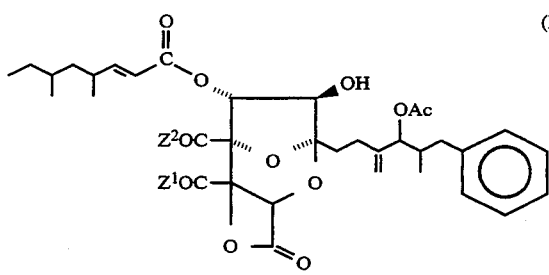

(III)

wherein:
$Z^1$ and $Z^2$ are each —$OR^6$; and
$R^6$ is independently selected at each occurence from
   (a) H,
   (b) $C_{1-5}$ alkyl, and
   (c) $C_{1-5}$ alkyl substituted with a member of the group consisting of
      (i) phenyl, (ii) phenyl substituted with methyl, methoxy, halogen (Cl, Br, I, F) or hydroxy, and
(iii) $C_{1-5}$ alkylcarbonyloxy,
(iv) $C_{6-10}$ arylcarbonyloxy,
(v) $C_{1-5}$ alkoxycarbonyloxy,
(vi) $C_{6-10}$ aryloxycarbonyloxy,

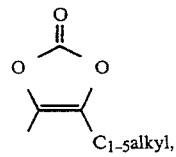
(vii)

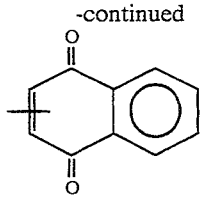
(viii)

(ix) or the groups (iii) to (vi) form a 5 to 10 membered mono- or bicyclic ring with $C_{1-5}$ alkyl, or a pharmaceutically acceptable salt thereof;

A third embodiment of this invention is further limited to compounds having the structural formula (IV) below:

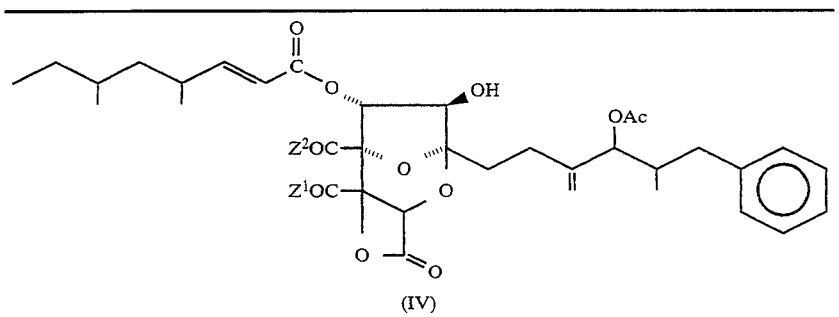

(IV)

| Compound No. | $Z^1$ | $Z^2$ |
|---|---|---|
| 1 | —OH | —OH |
| 2 | —OCH$_2$CH$_2$OCH$_3$ | —OH |
| 3 | —OCH$_2$OC(O)C(CH$_3$)$_3$ | —OH |
| 4 | —OCH$_3$ | —OH |
| 5 | —OH | —OCH$_3$ |
| 6 | —OCH$_2$C(O)N(CH$_3$)$_2$ | —OH |
| 7 | —OCH$_2$OC(O)CH$_3$ | —OH |
| 8 | —OCH$_2$OC(O)C(CH$_3$)$_3$ | —OH |
| 9 | —OCH(CH$_3$)OC(O)OCH$_2$CH$_3$ | —OH |
| 10 | —OCH(CH$_3$)OC(O)C(CH$_3$)$_3$ | —OH |
| 11 | (phthalide-O—) | —OH |
| 12 | (dioxolenone-OCH$_2$—) | —OH |
| 13 | —OH | (dioxolenone-OCH$_2$—) |
| 14 | —OH | —OCH$_3$ |
| 15 | —OH | —OCH$_2$OC(O)C(CH$_3$)$_3$ |
| 16 | —OH | —OCH$_2$OC(O)CH$_3$ |
| 17 | —OCH$_2$C(O)OC(CH$_3$)$_3$ | —OH |
| 18 | —O(CH$_2$)$_2$CH(CH$_3$)$_2$ | —OH |

In a fourth subclass of this embodiment are compounds of formula (I) with subgeneric formula (V) and wherein $R^1$ and $R^4$-$(A)_a$ are as described below.

TABLE 4

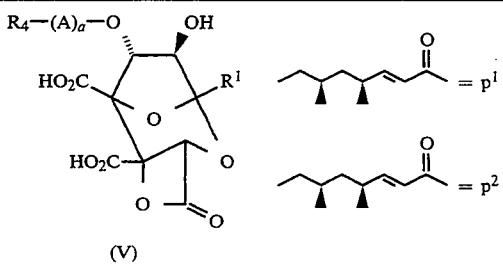

(V)

| Compound No. | $R^1$ | $R^4(A)_a$ |
|---|---|---|
| 19 | $-(CH_2)_2CH(CH_3)CH_2CH(CH_3)CH_2C_6H_5$ | $p^1$ |
| 20 | $-(CH_2)_2CH(CH_3)CH(OAc)CH(CH_3)CH_2C_6H_5$ | $p^2$ |

General Procedure for Preparation of B-lactones

Compounds IIA, IIB or IIC may be modified at C1 and or C6 positions as shown in EP 0 512 865 A2. The modified tricarboxylic acid derivatives may be treated with benzyl alcohol and an acid such as HCl to esterify the C3 position as its benzyl ester. The remaining C4 and C5 acid groups may be converted to tert-butyl esters by stirring with O-tert-butyl-N,N'-dialkyl isourea. Removal of the C3 benzyl group may be effected by stirring the triester with Pd/C and methyl cyclohexadiene in methanol. The C3 acid obtained as such may then be lactonized to the C4 hydroxy group by stirring the hydroxy acid first with a base such as N-methylmorpholine followed by aryl or alkyl sulfonyl halide such as benzenesulfonyl chloride or methyl sulfonyl chloride at $-20°$ to $60°$ C. for 2 to 16 hrs. Deprotection of the t-butyl groups is carried out by stirring the diesters with trifluoroacetic acid in methylene chloride. The diacid obtained as such could be modified at C4 or C5 position as shown in EP 0 512 865 A2. The C1 and or C6 side chain olefins of C4, C5 reduce diacids may be reduced catalytically by stirring the compounds in a solvent such as methanol with Pd/C over an atmosphere of hydrogen.

SCHEME 1

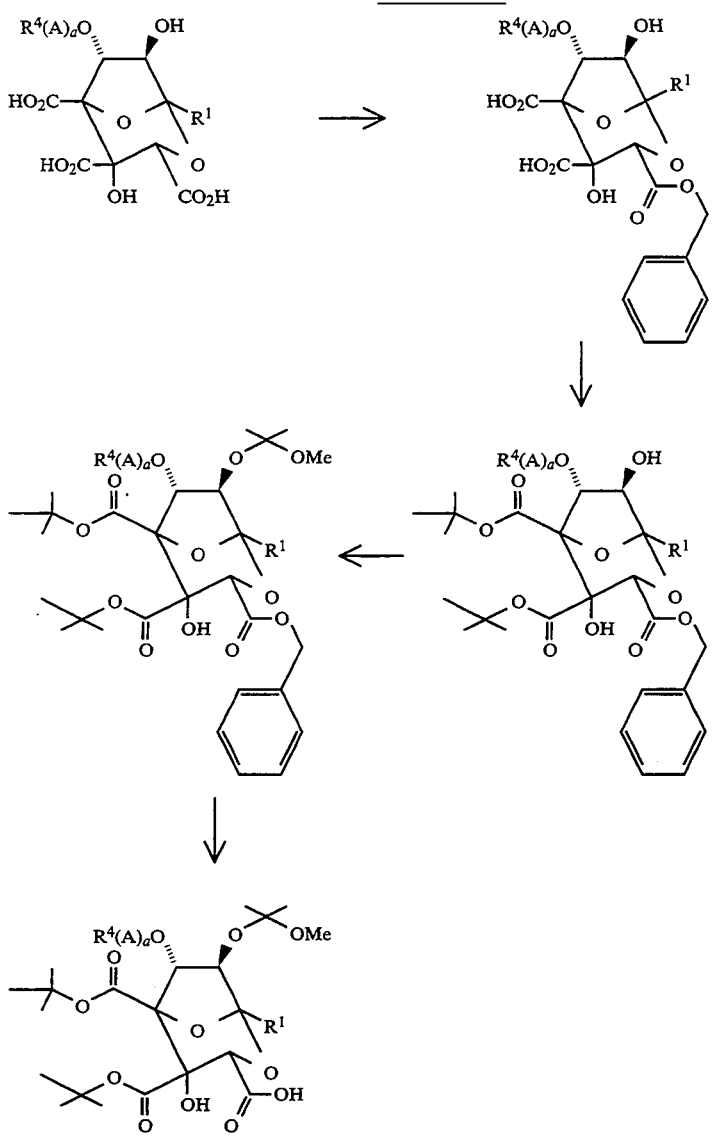

SCHEME 1 -continued

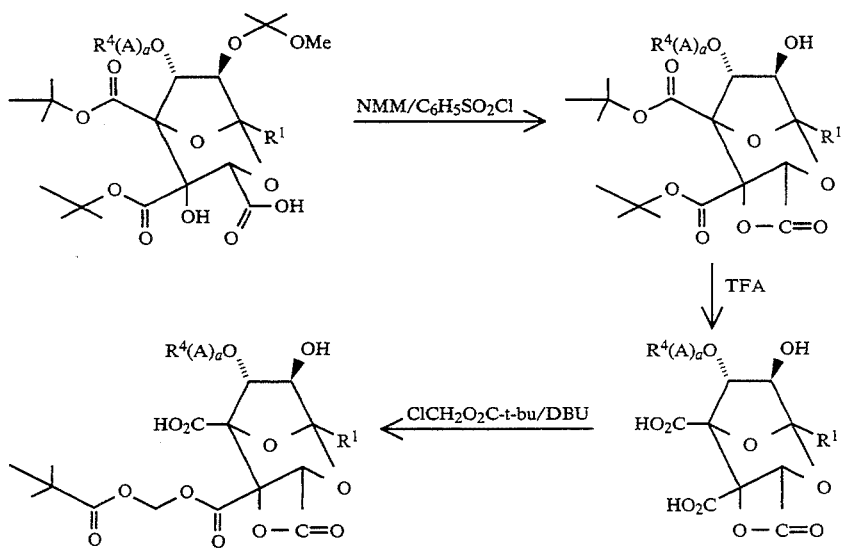

The compounds of formula (I) can be prepared from (1S,3S,4S,5R,6R,7R)-1-[(4S)-acetoxy-3-methylene-5-methyl-6-phenyl]hexyl-4,6,7-trihydroxy-6-O-(4,6-dimethyl-2-octenoyl)-2,8-dioxabicyclo[3.2.1]octane-3,4,5-tricarboxylic acid, hereafter referred to as Compound IIA, (1S,3S,4S,5R,6R,7R)-1-[4-hydroxy-3, 5-dimethyl-8-phenyl]oct-7-enyl-4,6,7-trihydroxy-6-O-(tetradeca-6,12-dienoyl)-2,8-dioxabicyclo[3.2.1]octane-3,4,5-tricarboxylic acid, hereafter referred to as Compound IIB and (1S,3S,4S,SR,6R,7R)-1-[4-acetoxy-5-methyl-6-phenyl]hexyl-4,6,7-trihydroxy-6-O-(6-methyl-9-phenyl-4-nonenoyl)-2,8-dioxabicyclo[3.2.1]octane-3,4,5-tricarboxylic acid, hereafter referred to as Compound IIC, the description below. Intermediates formed in the process of making the compounds of this invention are named as derivatives of Compounds IIA, IIB, and IIC. For example, the 3-t-butyl ester of compound IIA is named IIA-3-t-butyl ester. The preparation of Compounds IIA, IIB, and IIC have been described in U.S. Pat. No. 5,053,425, EP Publication No. 0 448 393 and U.S. Pat. No. 5,026,554, respectively.

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthetase which comprises the administration to a subject in need of such treatment a nontoxic therapautically effective amount of a compound represented by structural formula (I) and pharmaceutically acceptable salts thereof. Specifically, the compounds of this invention are useful in treating disease conditions such as, but not limited to, hypercholesterolemia which result from the action of the enzyme squalene synthetase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procains, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form. These salts may be prepared by standard procedures.

The compounds of this invention may also be administered in combination with other cholesterol lowering agents such as those which inhibit an enxymatic pathway in the biosynthesis of cholesterol. Example of such agents would include but are not limited to HMG-CoA reductase inhibitors, HMG-COA synthase inhibitors, and squalene expoxidase inhibitors. Illustrative of such inhibitors are lovastatin, simvastatin, pravastatin and fluvastatin.

Examples of HMG-CoA synthase inhibitors are the beta-lactone derivatives disclosed in U.S. Pat. Nos. 4,806,564; 4,816,477; 4,847,271; and 4,751,237; the beta-lactam derivatives disclosed in U.S. Pat. No. 4,983,597 and U.S. Ser. No. 07/540,992 filed Jun. 20, 1990; and the substituted oxacyclopropane analogues disclosed in European Patent Publication EP 0 411 703. Illustrative examples of squalene epoxidase inhibitors are disclosed in European Patent Publication EP 0 318 860 and in Japanese Patent Publication J02 169-571A. LDL-receptor gens inducer molecules are disclosed in U.S. Pat. application Ser. No. 07/670,640 filed Mar. 18, 1991. Other cholesterol lowering agents that may be administered include niacin, probucol, the fibtic acids: clofibrate and gemfibrozil, and LDL-receptor gens inducers. Representative of such combinations are those containing about 10–400 mg of a compound of formula (I) in combination with about 20–100 mg of an HMG-CoA reductase inhibitor, 20 to 200mg of a HMG-CoA synthase inhibitor, or 2 to 200mg of a squalene epoxidase inhibitor, or 250 to 1000 mg of probucol, or 600 to 1200 mg of gemfibrozil, or 1 to 2 g of clofibrate, or 3 to 6 g of niacin, or 20 to 300 mg of an LDL-receptor gens inducer.

The compounds of this invention may also be co-administered with pharmaceutically acceptable non-toxic cationic polymers capable of binding bile acids in a non-resorbable form in the gastrointestinal tract. Examples of such polymers include cholestyramine, colestipol and poly[methyl-(3-trimethyl)aminopropyl]iminotrimethylene dihalide. The relative amounts for co-administration of the compounds of this invention and these polymers is between 1:100 and 1:15,000 (w/w).

The intrinsic squalene synthase inhibitory activity of representative compounds of this invention was measured by the standard ill vitro protocol described below:

Preparation of Rat Liver Microsomes

Male, CHARLES RIVER CD ® rats (120 to 150 g) were fed a diet containing 0.1% lovastatin for 4 days. The livers from these rats were homogenized in 5 volumes (mL/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000 × g for 15 min. at 4° C., discarding the pellet each time. The supernatant was then centrifuged at 100,000 × g for 1 hr at 4° C. The resulting microsomal pellet was resuspended in a volume of the above homogenizing buffer equal to one-fifth the volume of the original homoSenate. This microsomal preparation has a protein concentration of about 7 mg/mL. The microsomal suspensions were stored in aliquots at −70° C. Squalene synthase activity in these aliquots is stable for a least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110,125–129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a WARING blender in 1 liter of 10 mM mercaptoethanol, 2 mM EDTA, 25 mM leupeptin, 0.005% phenylmethylsulfonyl fluoride, pH 7.0 containing 0.1 trypsin inhibitor units of apzotinin/mL. The homogenate was centrifuged at 20,000 × g for 20 min. The supernatant was adjusted to pH 5.5. with 6 N HOAc and centrifuged at 100,000 × g for 1 hour. This supernatant was adjusted to pH 7.0 with 3 N KOH and a 35–60% ammonium sulfate fraction taken. The 60% pellet was redissolved in 60 mL of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 mL of Buffer A and a 1 liter gradient from Buffer A to 100 mM potassium phosphate, 10 mM mercaptoethanol, 1 mMEDTA, pH 7.0. Fractions having a specific activity greater than 0.20 units/mg were combined, solid ammonium sulfate was added to bring to 60% saturation and pelleted. The pellet was dissolved in 8 mL 10 mM Tris, 10 mM β-mercaptoethanol pH 7.0 (Buffer B). The redissolved pellet was taken to 60% saturation with ammonium sulkate by adding 1.5 volumes of saturated ammonium sulfate in Buffer B. This ammonium sulfate suspension contained 3.5 units/mL with specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for a least 6 months.

Enzymatic Synthesis of [4-$^{14}$C]farnesyl-pyrophosphate

The solvent (ethanol: 0.15 N NH$_4$OH, 1:1) was removed from 55 mCi of [4-$^{14}$C]isopentenyl pyrophosphate (47.9 mCi/mmole) by rotary evaporation. Six hundred microliters of 100 mMTris, 10 mM MgCl$_2$, 4 mM dithiothreitol pH 7.5 was added and the solution was transferred to a 1.5 mL Eppendorf centrifUge tube. Geranyl-pyrophosphate, 250 mL of a 20 mM solution, and 50 mL of the ammonium sulfate suspension of prenyl transferase were-added to initiate the reaction. This incubation contained 5 mmoles of geranyl pyrophosphate, 1.15 mmoles of isopentenyl pyrophosphate, 6 mmoles of MgCl$_2$ of 0.18 units of prenyl transferass in a volume of 900 mL. The incubation was conducted at 37° C. During the incubation, the mix turned cloudy white as the newly formed magnesium complex of farnesyl pyrophosphate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 mL of 50 mM HEPES, 5 mM EDTA, pH 7.5. The yield was 50.7 mCi (92%) of [4-$^{14}$C]farnesyl pyrophosphate. The [4-$^{14}$C]farnesyl pyrophosphate was stored in aliquots at −70° C.

Squalene Synthase Assay

Reactions were performed in 16×125 mm screw cap test tubes. A batch assay mix was prepared from the following solution:

|   |   | mL per assay |
|---|---|---|
| 1. | 250 mM HEPES pH 7.5 | 20 |
| 2. | NaF 110 mM | 10 |
| 3. | MgCl$_2$ 55 mM | 10 |
| 4. | Dithiothreitol 30 mM | 10 |
| 5. | NADPH 10 mM (made fresh) | 10 |
| 6. | [4-$^{14}$C]farnesyl-pyrophosphate 47.9 mCi/mmole, and 0.025 mCi/3.0 mL | 3.0 |
| 7. | H$_2$O | 24 |

This assay mix was degassed under vacuum and flushed with $N_2$. Solutions of the squalene synthase inhibitors were prepared either in DMSO or MeOH and a 1:120 dilution of the microsomal protein was made with the original homogenizing buffer. For each reaction, 87 mL of the assay mix was taken with 3 mL of an inhibitor solution (DMSO or MeOH in the controls), warmed to 30° C. in a water bath and then the reaction was initiated by the addition of 10 mL of the 1:120 dilution of microsomal protein (0.6 µg protein total in the assay). The reactions were stopped after 20 minutes by the addition of 100 mL of a 1:1 mix of 40% KOH with 95% EtOH. The stopped mix was heated at 65° C. for 30 min., and cooled. Ten mL of heptane was added and the mix was vortexed. Two g of activated alumina was then added, the mix vortexed again, the alumina allowed to settle and 5 mL of the heptane layer was removed. Ten mL of scintillation fluid was added to the heptane solution and radioactivity was determined by liquid scintillation counting.

Percent inhibition is calculated by the formula:

$$1 - \frac{[Sample - Blank]}{[Control - Blank]} \times 100$$

Representative of the squalene synthase inhibitory character of the compounds of this invention are $IC_{50}$ the data below.

| Compound | Squalene Synthase $IC_{50}$ |
|---|---|
| 1 | 0.40 nM |

The present compounds also demonstrate broad spectrum antifungal activity as determined by broth dilution methods. The compounds are particularly active towards filamentous fungi and yeasts including *Candida albicans* and *Cryptococcus neoformans*. The sensitivity of filamentous fungi and yeast was determined using inhibitor dilution assays in microtiter format. The compounds were dissolved in 10% DMSO at 256 µg/mL and serially diluted in (DIFCO) Yeast Nitrogen Base supplemented with 1% glucose (YNBD) by two-fold dilutions yielding final drug concentrations ranging from 128–0.06 µg/mL. The wells were filled with 150 µL of inoculated media. Exponential phase *Candida* and *Cryptococcus* cells were diluted in YNBD such that the inoculum was $1.5-7.5 \times 10^3$ cells/mL. Aspergillus spores were harvested from a wellsporulated Sabouraud Dextrose Agar (SDA) slant in 0.01% Tween 80 and diluted into media to give an inoculum of $1 \times 10^3$ spores/mL. The microtiter dishes were incubated at 35° C. for 24 to 48 hours. The minimum inhibitory concentration (MIC) is defined as the lowest concentration to prevent visible growth after incubation for 24 to 48 hours at 35° C. for the yeasts and at 29° C. for the filamentous fungi. After recording the MIC of yeasts, plates were shaken on a (SARSTEDT) TPM2 shaker to resuspend the cells and a MIC-2000 inoculator (DYNATECH) was used to transfer a 1.5 µL sample from each well in the microplate to a spot in a single-well tray containing SDA. Inoculated trays were incubated at 35° C. and results were recorded at 24 h or 48 h (for Cryptococcus). The minimum fungicidal concentration (MFC) was defined as the lowest concentration of drug showing no growth or less than 4 colonies per spot. .

Thus the present invention is also directed to a method of inhibiting fungal growth which comprises the application to the area in which growth is to be controlled an antifungally effective amount of a compound of Formula (I). Additionally, the present invention is directed to a method of treating fungal infections which comprises the administration to an organism in need of such treatment a nontoxic therapeutically effective amount of a compound represented by the structural formula (I) and pharmaceutically acceptable salts thereof. Based on the above MIC data it is determined that generally from 2 to about 20 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The present invention is also directed to compounds of structural formula (I) which are inhibitors of farnesyl-protein transferase for inhibition of farnesylation of the oncogene protein Ras and the treatment of cancer.

The Ras gene is found activated in many human cancers, including colorectal carcinoma, exocrine pancreatic carcinoma, and myloid leukemias. Biological and biochemical studies of Ras action indicate that Ras functions like a G-regulatory protein, since Ras must be localized in the plasma membrane and must bind with GTP in order to transform cells (Gibbs, J. etal., *Microbiol. Rev.* 53:171-286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a ∂CAAX" or "Cys-Aaa$^1$-Aaa$^2$-Xaa" box (Aaa is an aliphatic amino acid, the Xaa is any amino acid) (Willumsen etal., *Nature* 310:583-586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey etal., *Proc. Natl. Acad. Sci.* USA 6:8323 (1989)). In addition, Ha-Ras and N-Ras are palmitoylated via formation of a thioester on a Cys residue near a C-terminal Cys farnesyl acceptor (Gutierrez etal., *EMBO J.* 8:1093-1098 (1989); Hancock et al., *Cell* 57:1167-1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg etal., *J. Biol. Chem.* 263:18236 (1988); Farnsworth etal., *J. Biol. Chem.* 264:20422 (1989)).

Inhibition of Ras farnesylation in vivo has been demonstrated with lovastatin (Merck & Co., Rahway, NJ) and compactin (Hancock etal., ibid; Casey et al., ibid; Schafer etal., *Science* 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss etal., *Cell,* 62:81-88 (1990); Schaber et al., *J. Biol. Chem.,* 265:14701-14704 (1990); Schafer etal., *Science,* 249:1133-1139 (1990); Manne et al., *Proc. Natl. Acad. Sci. USA,* 87:7541-7545 (1990)).

Inhibition of farnesyl-protein transferase and, thereby, of farnesylation of the Ras protein, blocks the ability of Ras to transform normal cells to cancer cells. Surprisingly, the compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs etal., *Proc. Natl. Acad. Sci USA* 86:6630-6634 (1989)). Cytosol-localized forms of Ras with normal GTPase activity do not act as inhibitors. Gibbs et al., ibid, showed this effect in Xenopus octyes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

FARNESYL-TKANSFERASE ASSAY I

Farnesyl-protein transferase (Ftase) from bovine brain was chromatographed on DEAE-Sephacel (Pharmacia, 0-0.8 M NaCl gradient elution), N-octyl agarose (Sigma, 0-0.6 M NaCl gradient elution), and a mono Q HPLC column (Pharmacia, 0-0.3 M NaCl gradient). Ras-CVLS at 3.5 μM, 0.25 μM [$^3$H]FPP, and the indicated compounds were incubated with this partially purified enzyme preparation. The Ftase data is a measurement of the ability of the test compound to inhibit Ras farnesylation in Vitro.

FARNESYL-TRANSFERASE ASSAY II

Farnesyl-protein transferase (Ftase) from bovine brain was chromatographed on DEAE-Sephacel (PHARMACIA, 0-0.8 M NaCl gradient elution), N-octyl agarose (SIGMA, 0-0.6 M Nacl gradient elution), and a mono Q HPLC column (PHARMACIA, 0-0.3 M NaCl gradient). Ras-CVLS at 1.0 μM, 0.5 μM [$^3$H]FPP, and the indicated compounds were incubated with this partially purified enzyme preparation. The Ftase data is a measurement of the ability of the test compound to inhibit Ras farnesylation in vitro.

The pharmaceutical compositions containing the compounds of structural formula (I) inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone, or preferably, in combination with pharmaceutically-acceptable carriers or diluents, optionally with known-adjuvants, such as alum, in a pharmaceutical composition, according to standard pharmaceutical practice. The compounds can be administered orally or parenterally, including intravenous, intramuscular, intraperitioneal, subsutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. .If desired, certain sweetening and-/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a method of the treatment of cancer, comprising the administration of a pharmaceptical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in a amount between about 0.1 mg/kg of body weight of about 20 mg/kg of body weight of a mammal per day, preferably of between 0.5 mg/kg of body weight to about 10 mg/kg of body weight of a mammal per day.

The following examples illustrate the preparation of the compounds of formula (I) and their incorporation into pharmaceutical compositions and, as such, are not to be considered as limiting the invention set forth in the claims appended hereto.

EXAMPLE 1

IIA-β-Lactone 4.5-di-t-hutyl ester

Step A: Preparation of IIA-3-Benzyl ester

Acetyl chloride (0.4 mL) was added to benzyl alcohol (10 mL) and the reaction mixture stirred at room temperature for 30 min. Solid IIA (1 g) was added and the reaction mixture stirred for additional six hours. The mixture was degassed, poured into acetonitrile-water mixture (200 mL, 38%), filtered through a bed of C-8 reverse phase column (30 g. Baker) to remove unreacted benzyl alcohol, and then washed several times with acetonitrile (400 mL). Evaporation of the acetonitrile fraction under vacuum gave IIA-3-benzyl ester (86% pure by HPLC). Further purification was carried out by reverse phase chromatography (C-8 Baker, 58% acetonitrile in water). $^1$NMR (300 MHz, CD$_3$OD) δ7.46–7.12 (m, 10 H), 6.88(dd, J=8.9,18 Hz, 1H), 6.38(brs, 1H), 5.48(d, J=15 Hz, 1 H), 5.42(s, 1 H), 5.23(dd, J=14, 5.1 Hz, 2 H), 5.14(s,1 H), 5.04 & 5.00(2s, 2 H), 4.06(brs, 1 H), 2.71(m, 1H), 2.54–2.00(m, 7 H), 2.12(s, 3 H), 1.50–1.1(m, 6 H), 1.07(d, J=6 Hz, 3H), 0.90(m, 9H); FAB m/e 793(M+2Li), 799 (M+3Li).

Step B: Preparation of IIA-3-Benzyl-4,5-di-t-butyl ester

A solution of IIA-3-benzyl ester (100 mg) dissolved in methylene chloride (2 mL) was treated with O-t-butyl-N,N'-diisopropylisourea (300 mg) and stirred at 40° C. for 2 days. The reaction mixture was cooled to room temperature, concentrated and filtered through a bed of silica (25% ethyl acetate in hexane) to yield pure IIA-3-benzyl-4,5-di-t-butyl-ester. $^1$NMR (400 HHz, CDCl$_3$) δ7.35–7.08 (m, 10H), 6.88(dd, J=8.4,16 Hz, 1H), 5.97(d, J=1Hz, 1H), 5.75(d, J=16 Hz, 1H), 5.42(s, 1H) 5.16(dd, J=12, 6.4 Hz, 2H), 5.06(br s, 1H), 4.94(br s, 2H), 4.00(br s, 1H), 2.96(d, J=2 Hz, 1H), 2.66(m, 1H), 2.5–2.2(m, 5H).

Step C: Preparation of IIA-7-(1-Methyl-1-methoxyethyl ether)-3-benzyl-4.5-di-t-butyl ester A solution of IIA-7-(1-methyl-1-methoxyethyl ether)-3-benzyl ester (100 mg) dissolved in methylene chloride (2 mL) was treated with O-t-butyl-N,N'-diisopropylisourea (300 mg) and stirred at 40° C. for 2 days. The reaction mixture was cooled to room temperature, concentrated and filtered through a bed of silica (25% ethyl acetate in hexane) to yield pure IA-7-(1-methyl-1-methoxyethyl ether)-3-benzyl-4,5-di-t-butyl-ester. $^1$NMR (400 Hz, CD$_3$OD) δ7.4–7.12(m, 10H), 6.88(dd, J=8.5,15.6 Hz, 1H), 6.48(d, J=1.85 Hz, 1H), 5.84(d, J=15.6Hz, 1H), 5.29(s, 1H), 5.23 and 5.10(ea d, J=12 Hz, ea 1H), 5.07(d, J=4.8 Hz, 1H), 4.99 and 4.99(ea s, ea 1H), 4.23(d, J=1.85 Hz, 1H), 3.18(s, 3H), 2.09(s, 3H), 1.52 and 1.39(ea s, ea 9H), 1.34(s), 1.26(s), 1.02(d, J=6.7 Hz, 3H), 0.9–0.8(m, 9H).

Step D: Preparation of IIA-g-(1-Methyl-1-methoxyethyl ether)-4,5-di-t-butyl ester To a solution of IIA-7-(1-methyl-1-methoxyethyl ether)-3-benzyl-4,5-di-t-butyl ester (100 mg) in methanol (4 mL) was added methyl cyclohexadiene (200 μL) and Pd/C (50 mg). The reaction mixture was stirred at 30°–35° C. for 1.5 h and filtered over Celite ™. The filtrate was evaporated under vacuum to give IIA-7-(1-methyl-1-methoxyethyl ether)-4, 5-di-t-butyl ester. $^1$H NMR (400 Hz, CD$_3$OD) δ7.30–7.10 (m,5H), 6.92 (dd, J=8.4,15.6 Hz, 1H), 6.50 (d, J=1.7 Hz, 1H), 5.85 (d, J=15.6 Hz, 1H), 5.19 (s, 1H), 5.08 (d, J=4.78 Hz, 1H), 5.02 and 4.97 (ea s, ea 1H), 4.25 (d, J=1.7 Hz, 3H), 3.19 (s, 3H), 2.10 (s, 3H), 1.63 and 1.40 (ea s, ea 9H), 1.35 (s), 1.26 (d, J=5.8 Hz, 3H), 1.02 (d, J=6.73 Hz, 3H), 0.88–0.82 (m, 9H).

Step E: Preparation of IIA-β-Lactone-4,5-di-t-butyl ester

To 700 mg of IIA-7-(1-methyl-1-methoxyethylether)-4,5-di-t-butyl ester in 4 mL of methylene chloride, 100 μL of N-methyl morpholine was added and stirred at room temperature for about 10 minutes. The solution was cooled to −20° C. and treated with 150 μL of benzenesulfonyl chloride followed by 4 mL tetrahydrofuran and 200 μL DBU and stirred overnight at room temperature. Ethyl acetate/2N HCl workup the following day gave the C7 deprotected β-lactone. $^1$H NMR (400 MHz, CD$_3$OD) δ7.30–7.10(m, 5H), 6.92(dd, J=8.16 Hz, 1H), 6.58(d, J=2.6 Hz, 1H), 5.84(d, J=16 1H), 5.45(s, 1H), 5.04(d, J=4.5 Hz, 1H) 4.97, 4.96(each s, each 1H), 4.00(d, J=2.6 Hz, 1H), 2.65(m, 1H), 2.5–2.2(m, 3H), 2.10(s, 3H), 1.62(s, 9H), 1.40(s, 9H), 1.03(d, J=8 Hz, 3H), 0.86(m, 9H)

MS-FAB m/e 783

IR ν C=O 1865 cm$^{-1}$

EXAMPLE 2

IIA-β-Lactone 50 mg of IIA-β-lactone-di-t-butyl ester prepared above was stirred overnight with 1.5 mL of methylene chloride and 0.5 mL of TFA and evaporated to yield the desired product. $^1$H NMR (400 MHz, CDCl$_3$) δ7.3–7.1(m, 5H), 6.87(dd, J=8.4, 16 Hz, 1H), 6.54(d, J=3.2 Hz, 1H), 5.81(d, J=16 Hz, 1H), 5.52(s, 1H) 5.03(d, J=4.9 Hz, 1H), 4.97 4.95(ea s, ea 1H), 3.95(d, J=3.0, 1H), 2.66(m, 1H), 2.5–2.2(m, 5H), 2.10(s, 3H), 1.03(d, J=8 Hz, 3H), 0.87(m, 9H)

EXAMPLE 3

Preparation of an Ammonium Salt

A 0.1 mmol sample of the free acid of a compound of formula (I) is dissolved in 10 mL ethyl acetate. The resulting solution is saturated with gaseous ammonia and the ammonium salt precipitates from solution.

EXAMPLE 4

Preparation of a Potassium Salt

A solution of 0.1 mmol of the free acid of a compound of formula (I) in 10 mL methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion, the sodium and lithium salts can be formed.

EXAMPLE 5

Preparation of a Calcium Salt

A solution of 0.1 mmol of the free acid of a compound of formula (I) in 20 mL 6:4 methanol:water is treated with an aqueous solution of 0.1 mmol of calcium hydroxide. The solvents are evaporated to give the corresponding calcium salt.

EXAMPLE 6

Preparation of an Ethylenediamine Salt

A solution of 0.1 mmol of the free acid of a compound of formula (I) in 10 mL of methanol is treated with 0.1 mmol of ethylenediamine. Evaporation of the solvent affords the ethylenediamine salt. The procedure can also be applied to the preparation of the N,N''-dibenzylethylenediamine salt.

EXAMPLE 7

Preparation of a Tris(hydroxymethyl)aminomethane Salt

To a solution of 0.1 mmol of the free acid of a compound of formula (I) in 10 mL of methanol is added from 0.1 to 0.3 mmol of tris(hydroxymethyl)aminomethane dissolved in 10 ml of methanol. Evaporation of the solvent gives a corresponding salt form, the exact composition of which is determined by the molar ratio of amine added. Similarly prepared are the salts of L-ornithine, L-lysine, and N-methylglutamine.

EXAMPLE 8

Preparation of an L-arzinine Salt

A solution of 0.1 mmol of the free acid of a compound of formula (I) in 20 ml of 6:4 methanol: water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglutamine.

EXAMPLE 9

Preparation of the trimethyl ester of a Compound of Formula (I) (Method I)

TO 5 mg of the free acid of a compound of formula (I) in methanol (5 mL) is added 2 mL of freshly distilled diazomethane in ether (2.05 M). After 5 minutes the solvent is removed to afford trimethyl ester as an oil.

EXAMPLE 10

Preparation of the trimethyl ester of a Compound of Formula (I) (Method II)

To 0.6 mg of the free acid of a compound of formula (I) in 1 mL diethyl ether at 0° C. is added ethereal cyanamide dropwise until the solution remains yellow. The solution is evaporated under a Stream of nitrogen to yield the trimethyl ester.

EXAMPLE 11

Preparation of the tribenzylester of a Compound of Formula (I)

To a solution of 5 mg of the free acid of a compound of formula (I) in 0.5 mL tetrahydrofuran (THF) is treated at room temperature with 3 equivalents of N,N'-diisopropyl-O-benzyl isourea for 18 hours. The reaction mixture is then chilled to −15° C., and filtered to remove the urea. The fiftrate is concentrated under reduced pressure to yield the tribenzyl ester.

The method of Example 11 is also suitable for the preparation of other ester derivatives such as 1) ethyl and the other lower alkyls, and 2) substituted benzyl esters, using the appropriately substituted isourea. By varying the number of equivalents of the substituted isourea used, the mono-, di-, and tri-substituted esters may be selectively prepared.

EXAMPLE 12

Preparation of the mono-, di- and tri-Kanebo Esters

To a stirred solution of the free acid of a compound of Formula (I) (100 mg) in 2 mL THF at 0° C. under $N_2$ is added 1,8-diazabicyclo[5.4.0]undec-7-ene (DBU, 27.4 mL, 0.183 mmol) dropwise. After stirring at 0° C. for 10 min, followed by an additional 10 minutes at room temperature, 4-bromomethyl-5-methyl-1,3-dioxolen-2-one (Kanebo, 58.95 mg, 0.305 mmol) is added dropwise, stirred for 10 minutes, then heated at 60° C. from 2 days. Products are isolated by evaporation, prep HPLC on a reverse phase column to give mixtures of the mono, di, and tri Kanebo esters. By varying the number of equivalents of DBU and the bromo- compound used, a more selective preparation of mono-, di- or tri- esters may be accomplished.

EXAMPLE 13

Preparation Of the tri-pivaloyl ester

To 100 mg of the free acid of a compound of Formula (I) in 3 mL refluxing acetonitrile, 75 microliters of DBU and 72 microliters of chloromethyl pivalate is added and refluxed until completion of the reaction. The tri-pivaloyl ester is separated from the mono- and di- pivaloyl esters by reverse phase HPLC, eluted with acetonitrile-water. By varying the number of equivalents of DBU and the chloromethyl pivalate used, the mono and di esters may be selectively prepared.

EXAMPLE 14

Oral Composition

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

What is claimed is:

1. A compound of structural formula (I)

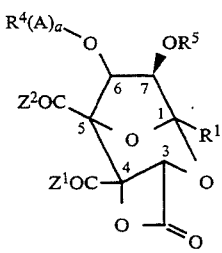

wherein:
a is 0 or 1;
A is —C(O)—, —NR$^3$—C(O)—, or —OC(O)—;
R$^1$ is:
 (1) C$_{1-20}$ alkyl,
 (2) substituted C$_{1-20}$ alkyl wherein one or more of the carbons is substituted with X$^3$;
 (5) aryl substituted with X and Y;
 (6) heteroaryl substituted with X and Y;
 (7) C$_{2-20}$ alkenyl wherein alkenyl contains one or more double bonds;
 (8) substituted C$_{2-20}$ alkenyl wherein alkenyl contains one or more double bonds and wherein one or more of the carbons is substituted with X$^3$;
 (9) C$_{2-20}$ alkenyl wherein alkenyl contains one or more double bonds and one or more of the nonolefinic carbons is replaced by —NR$^3$—, —O— or —S(O)$_n$—;
 (11) C$_{3-10}$ cycloalkyl;
 (12) substituted C$_{3-10}$ cycloalkyl in which one or more of the carbon atoms is substituted with:
  (a) halogen,
  (b) hydroxy,
  (c) R$^3$R$^3$N—,
  (d) R$^2$O—,
  (e) R$^2$O—C(O)—,
  (f) R$^3$—C(O)—O—,
  (g) oxo,
  (h) C$_{3-10}$ cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) R$^3$—C(O)—NR$^3$—,
  (n) R$^3$R$^3$N—C(O)—,
  (o) C$_{1-10}$ alkylS(O)$_n$—,
  (p) C$_{1-10}$ alkyl,
  (q) —CO$_2$H,
  (r) —vinylidene,
  (s) R$^3$—C(O)—,
  (t) R$^2$O—C(O)—O—,
  (u) R$^3$R$^3$N—C(O)—O—, or
  (v) R$^2$O—C(O)—NR$^3$—;
each R$^2$ is independently:
 (1) C$_{1-10}$ alkyl;
 (2) aryl substituted with X and Y;
 (3) arylC$_{1-4}$ alkyl wherein aryl is substituted with X and Y;
 (4) heteroaryl wherein heteroaryl is substituted with X and Y;
 (5) heteroarylC$_{1-4}$ alkyl— wherein heteroaryl is substituted with X and Y;
 (6) heterocycloalkylC$_{1-4}$ alkyl—;
 (7) C$_{2-10}$ alkenyl;
 (8) arylC$_{2-10}$ alkenyl wherein aryl is substituted with X and Y; or
 (9) C$_{3-10}$ alkynyl;
each R$^3$ is independently:
 (1) C$_{1-10}$ alkyl;
 (2) aryl substituted with X and Y;
 (3) arylC$_{1-4}$ alkyl wherein aryl is substituted with X and Y;
 (4) heteroaryl wherein heteroaryl is substituted with X and Y;
 (5) heteroarylC$_{1-4}$ alkyl— wherein heteroaryl is substituted with X and Y;
 (6) heterocycloalkylC$_{1-4}$ alkyl—;
 (7) C$_{2-10}$ alkenyl;
 (8) arylC$_{2-10}$alkenyl wherein aryl is substituted with X and Y;
 (9) C$_{3-10}$ alkynyl;
 (10) hydrogen; or
 (11) C$_{1-5}$ alkyl substituted with X$^1$;
R$^4$ is:
 (1) C$_{1-20}$ alkyl;
 (2) substituted C$_{1-20}$ alkyl in which one or more carbon atoms is substituted with X$^3$;
 (3) C$_{1-20}$ alkyl wherein one or more of the carbons is replaced by —NR$^3$—, —O—, or —S(O)$_n$—;
 (4) substituted C$_{1-20}$ alkyl wherein one or more of the carbons is replaced by —NR$^3$—, —O— or —S(O)$_n$— and wherein one or more carbon atoms is substituted with X$^3$;

(5) aryl substituted with X and Y;
(6) heteroaryl substituted with X and Y;
(7) $C_{2-20}$ alkenyl wherein alkenyl contains one or more double bonds;
(8) substituted $C_{2-20}$ alkenyl wherein alkenyl contains one or more double bonds and wherein one or more of the carbons is substituted with $X^3$;
(9) $C_{2-20}$ alkenyl wherein alkenyl contains one or more double bonds and one or more of the nonolefinic carbons is replaced by $—NR^3—$, $—O—$ or $—S(O)_n—$;
(10) substituted $C_{2-20}$ alkenyl wherein alkenyl contains one or more double bonds and one or more of the nonolefinic carbons is replaced by $—NR^3—$, $—O—$ or $—S(O)_n—$ and wherein one or more of the carbon atoms is substituted with $X^3—$;
(11) $C_{3-10}$ cycloalkyl;
(12) substituted $C_{3-10}$ cycloalkyl in which one or more of the carbon atoms is substituted with $X^3$; or
(13) hydrogen;

$R^5$ is:
(1) hydrogen;
(2) $C_{1-10}$ alkyl;
(3) aryl substituted with X and Y;
(4) aryl$C_{1-4}$ alkyl, wherein aryl is substituted with X and Y;
(5) $R^2O—C(O)—$;
(6) $C_{3-10}$ cycloalkyl;
(7) $R^3—C(O)—$; or
(8) $R^3R^3N—C(O)—$; aryl including X, Y substitution is:

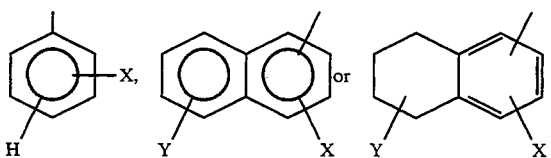

heteroaryl including X, Y substitution is

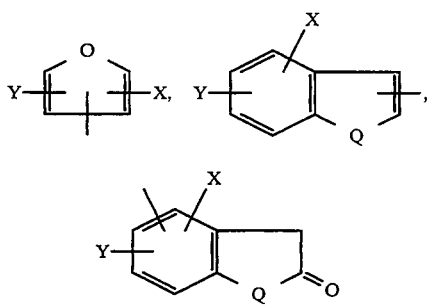

wherein:
Q is $—O—$;
heterocycloalkyl is:

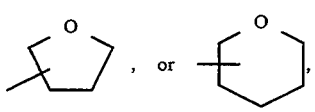

X and Y are each independently:
(1) hydrogen;
(2) hydroxy;
(3) halogen;
(4) trifluoromethyl;
(5) $C_{1-10}$ alkyl;
(6) aryl substituted with $X^1$ and $Y^1$;
(7) $R^2O—$;
(8) arylcarbonyloxy—, wherein aryl is substituted with $X^1$ and $Y^1$;
(9) $R^3—C(O)—O—$;
(10) $—CO_2R^2$;
(11) $—CO_2H$; or
(12) nitro;

$X^1$ and $Y^1$ are each independently:
(1) hydrogen;
(2) hydroxy;
(3) halogen;
(4) trifluoromethyl;
(5) $C_{1-4}$ alkyl;
(6) $R^2O—$;
(7) $R^3—C(O)—O—$;
(8) $—CO_2R^2$;
(9) $—CO_2H$; or
(10) nitro;

each $X^3$ is independently:
(1) halogen
(2) hydroxy,
(3) $R^3R^3N—$,
(4) $R^2O—$,
(5) $R^2O—C(O)—$,
(6) $R^3—C(O)—O—$,
(7) oxo,
(8) $C_{3-10}$ cycloalkyl,
(9) aryl substituted with X and Y,
(10) heteroaryl substituted with X and Y,
(11) heterocycloalkyl,
(12) aryl $S(O)_n$, wherein aryl is substituted with X and Y,
(13) $R^3—C(O)—NR^3—$,
(14) $R^3R^3N—C(O)—$,
(15) $—CO_2H$,
(16) —vinylidene,
(17) $R^3—C(O)—$,
(18) $R^2O—C(O)—O—$,
(19) $R^3R^3NOC(O)—O—$, or
(20) $R^2O—C(O)—NR^3—$;

n is 0, 1 or 2;

$Z^1$ and $Z^2$ are each independently:
(1) $—OR^6$;
(2) $—SR^6$; or
(3) $—NR^6R^6$;

each $R^6$ is independently:
(1) $C_{1-20}$ alkyl;
(2) substituted $C_{1-20}$ alkyl in which one or more of the carbon atoms is substituted with $X^3$;
(3) $C_{-20}$ alkyl wherein one or more of the carbons is replaced by $—NR^3—$, $—O—$, or $—S(O)_n—$;
(4) substituted $C_{-20}$ alkyl wherein one or more of the carbons is replaced by $—NR^3—$, $—O—$ or $—S(O)_n—$ and wherein one or more of the carbon atoms is substituted with $X^3$;
(5) $C_{2-20}$ alkenyl wherein alkenyl contains one or more double bonds;
(6) substituted $C_{2-20}$ alkenyl wherein alkenyl contains one or more double bonds and wherein one or more of the carbons is substituted with:
(a) halogen,
(b) hydroxy,
(c) $R^3R^3N—$,
(d) $R^2O—$,
(e) $R^2O—C(O)—$, (f) R³—C(O)—O—,
(g) oxo,
(h) C₃₋₁₀ cycloalkyl,
(i) aryl substituted with X and Y,
(j) heteroaryl substituted with X and Y,
(k) heterocycloalkyl,
(l) aryl S(O)ₙ—, wherein aryl is substituted with X and Y,
(m) R³—C(O)—NR³—,
(n) R³R³N—C(O)—,
(o) —CO₂H,
(p) —vinylidene,
(q) R³—C(O)—,
(r) R²O—C(O)—O—,
(s) R³R³N—C(O)—O—,
(t) R²O—C(O)—NR³—, or
(u) —OC(O)O—, which forms a five-membered ring:

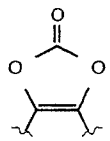

P2 with adjacent olefinic carbons;
(7) C₂₋₂₀ alkenyl wherein alkenyl contains one or more double bonds and one or more of the nonolefinic carbons is replaced by —NR³—, —O— or —S(O)ₙ—;
(8) substituted C₂₋₂₀ alkenyl wherein alkenyl contains one or more double bonds and one or more of the nonolefinic carbons is replaced by —NR³—, —O— or —S(O)ₙ— and wherein one or more of the carbon atoms is substituted with:
(a) halogen
(b) hydroxy,
(c) R³R³N—,
(d) R²O—,
(e) R²O—C(O)—,
(f) R³—C(O)—O—,
(g) oxo,
(h) C₃₋₁₀ cycloalkyl,
(i) aryl substituted with X and Y,
(j) heteroaryl substituted with X and Y,
(k) heterocycloalkyl,
(l) aryl S(O)ₙ—, wherein aryl is substituted with X and Y,
(m) R³—C(O)—NR³—,
(n) R³R³N—C(O)—,
(o) —CO₂H,
(p) —vinylidene,
(q) R³—C(O)—,
(r) R²O—C(O)—O—,
(s) R³R³N—C(O)—O—,
(t) R²O—C(O)—NR³— or
(u) —OC(O)O—, which forms a five-membered ring:

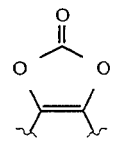

with adjacent olefinic carbons;
(9) C₂₋₂₀ alkynyl wherein alkynyl contains one or more triple bonds;
(10) substituted C₂₋₂₀ alkynyl wherein alkynyl contains one or more triple bonds and wherein one or more of the carbons is substituted with X³;
(11) C₂₋₂₀ alkynyl wherein alkynyl contains one or more triple bonds and one or more of the saturated carbons is replaced by —NR³—, —O— or —S(O)ₙ—;
(12) substituted C₂₋₂₀ alkynyl wherein alkynyl contains one or more double bonds and one or more of the saturated carbons is replaced by —NR³—, —O— or —S(O)ₙ— and wherein one or more of the carbon atoms substituted with X³;
(13) aryl substituted with X and Y;
(14) heteroaryl substituted with X and Y;
(15) C₃₋₅ cycloalkyl;
(16) substituted C₃₋₅ cycloalkyl in which one or more of the carbon atoms is substituted with:
(a) R³O—, or
(b) R³R³N—; or
(17) hydrogen; or a pharmaceutically acceptable salt.

2. The compound according to claim 1 selected from:

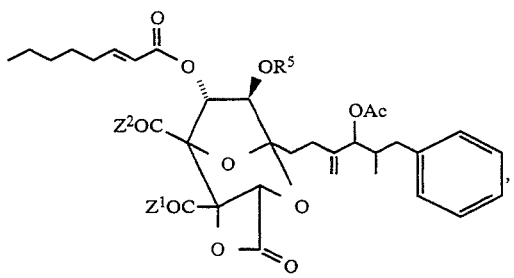

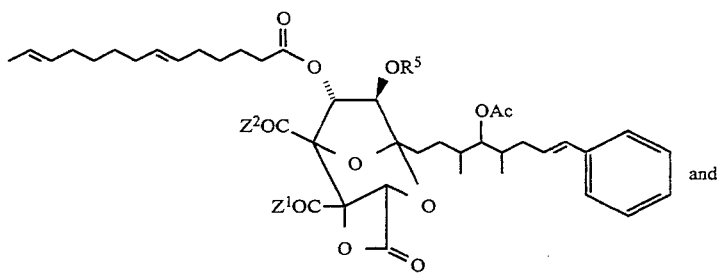

and

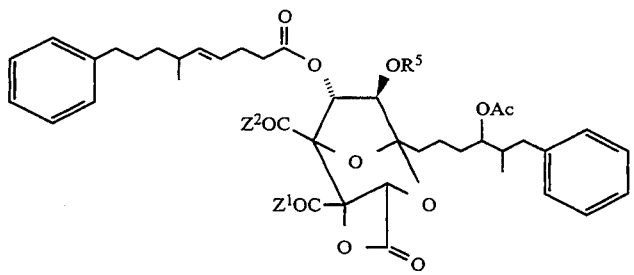

3. The compound according to claim 1 of structural formula (III):

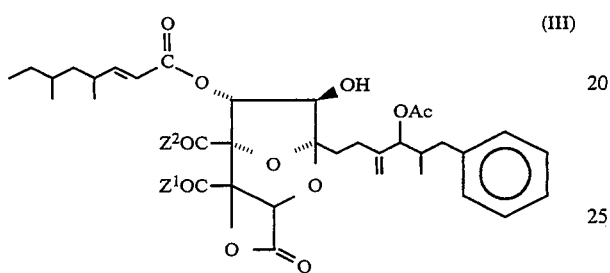

wherein:
$Z^1$ and $Z^2$ are each $-OR^6$; and
each $R^6$ is
(a) H,
(b) $C_{1-5}$ alkyl, and
(c) $C_{1-5}$ alkyl substituted with a member of the group consisting of
(i) phenyl,
(ii) phenyl substituted with methyl, methoxy, halogen (Cl, Br, I, F) or hydroxy, and
(iii) $C_{1-5}$ alkylcarbonyloxy,
(iv) $C_{6-10}$ arylcarbonyloxy,
(v) $C_{1-5}$ alkoxycarbonyloxy,
(vi) $C_{6-10}$ aryloxycarbonyloxy,

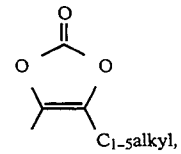

(vii)

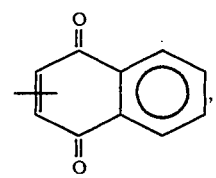

(viii)

(ix) or the groups (iii) to (vi) form a 5 to 10 membered mono- or bicyclic ring with $C_{1-5}$ alkyl, or a pharmaceutically acceptable salt thereof.

4. The compound according to claim 1 of structural formula (IV)

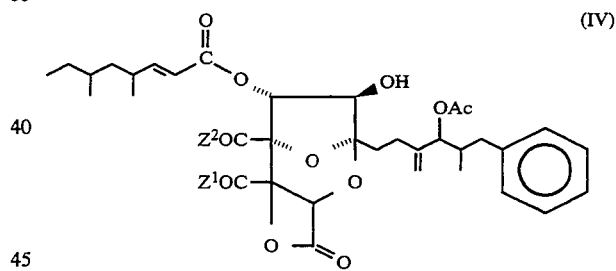

wherein $Z^1$ and $Z^2$ are as shown below:

| Compound No. | $Z^1$ | $Z^2$ |
|---|---|---|
| 1 | —OH | —OH |
| 2 | —OCH₂CH₂OCH₃ | —OH |
| 3 | —OCH₂OC(O)C(CH₃)₃ | —OH |
| 4 | —OCH₃ | —OH |
| 5 | —OH | —OCH₃ |
| 6 | —OCH₂C(O)N(CH₃)₂ | —OH |
| 7 | —OCH₂OC(O)CH₃ | —OH |
| 8 | —OCH₂OC(O)C(CH₃)₃ | —OH |
| 9 | —OCH(CH₃)OC(O)OCH₂CH₃ | —OH |
| 10 | —OCH(CH₃)OC(O)C(CH₃)₃ | —OH |
| 11 | 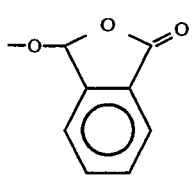 | —OH |

-continued

| Compound No. | $Z^1$ | $Z^2$ |
|---|---|---|
| 12 | —OCH₂—C(CH₃)=... (methylenedioxy cyclic structure) | —OH |
| 13 | —OH | —OCH₂—C(CH₃)=... (methylenedioxy cyclic structure) |
| 14 | —OH | —OCH₃ |
| 15 | —OH | —OCH₂OC(O)C(CH₃)₃ |
| 16 | —OH | —OCH₂OC(O)CH₃ |
| 17 | —OCH₂C(O)OC(CH₃)₃ | —OH |
| 18 | —O(CH₂)₂CH(CH₃)₂ | —OH. |

5. The compound according to claim 1 of structural formula (V)

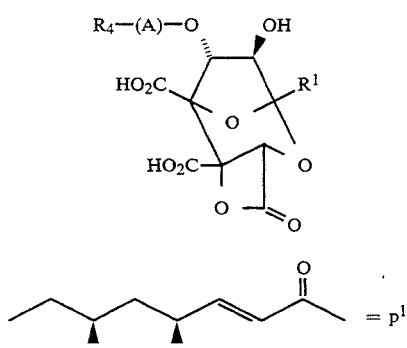

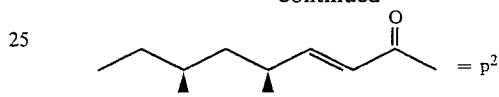

wherein $R^1$ and $R_4$-(A)$_a$— are as shown below:

| Compound No. | $R^1$ | $R^4(A)_a$ |
|---|---|---|
| 19 | —(CH₂)₂CH(CH₃)CH₂CH(CH₃)CH₂C₆H₅ | $p^2$ |
| 20 | —(CH₂)₂CH(CH₃)CH(OAc)CH(CH₃)CH₂C₆H₅ | $p^2$ |

6. A pharmaceutical composition comprising a non-toxic therapeutically effective amount of a compound of claim 1 and a pharmaceutically acceptable carrier.

7. A pharmaceutical composition comprising a non-toxic therapeutically effective amount of a compound of claim 1 in combination with a pharmaceutically acceptable non-toxic cationic polymer capable of binding bile acids in a non-resorbable form in the gastrointestinal tract and a pharmaceutically acceptable carrier.

* * * * *

UNITED STATES PATENT AND TRADEMARK OFFICE
CERTIFICATE OF CORRECTION

PATENT NO. : 5,447,717

DATED : 9/5/95

INVENTOR(S) : Tesfaye Biftu

It is certified that error appears in the above-identified patent and that said Letters Patent is hereby corrected as shown below:

In the abstract of the title page, line 4 after the formula, change "transferass" to -- transferase --.

In Col. 1, at the eighth paragraph, line 48, change "transferass" to -- transferase --.

In Col. 1, at the ninth paragraph, line 51, change "transferass" to -- transferase --.

In Col. 16, at the first paragraph, line 17, change "ammonium sulkate" to -- ammonium sulfate --.

In Col. 19, at the sixth paragraph, line 54, change "vivohas" to -- vivo has --.

In Col. 20, line 35, amend the title "FARNESYL-TKANSFERASE ASSAY I" to -- FARNESYL-TRANSFERASE ASSAY I --.

In Col. 21, at the second paragraph, line 21, delete ".If" and substitute therefor -- If --.

In Col. 24, at Example 10, line 47, change "Stream" to -- stream --.

In Claim 1, at Col. 29, line 25, before the phrase "with adjacent olefinic carbons;", delete P2.

In the structure of Claim 5, at Col. 33, line 34, delete, "$R_4$-(A)-O" and substitute therefor -- $R_4-(A)_a-O$ --.

Signed and Sealed this

Twenty-sixth Day of December, 1995

*Attest:*

BRUCE LEHMAN

*Attesting Officer*  *Commissioner of Patents and Trademarks*